United States Patent [19]

Alaimo et al.

[11] 4,221,730

[45] Sep. 9, 1980

[54] 3-[[(4-AMINOPHENYL)SULFONYL]AMINO]-N-[DIAMINOPHOSPHINYL]-BENZAMIDE

[75] Inventors: Robert J. Alaimo; Ronald J. Storrin; Ozra E. Millner, Jr., all of Norwich, N.Y.

[73] Assignee: Morton-Norwich Products, Inc., Norwich, N.Y.

[21] Appl. No.: 60,892

[22] Filed: Jul. 26, 1979

[51] Int. Cl.² ............... A61K 31/63; A61K 31/66; C07C 143/80
[52] U.S. Cl. .................. 260/397.7 R; 260/551 P; 260/556 B; 260/543 P; 424/228; 424/320; 424/321
[58] Field of Search ............... 260/397.7 R, 551 P, 260/556 B

[56] References Cited

U.S. PATENT DOCUMENTS

| | | | |
|---|---|---|---|
| 3,321,516 | 5/1967 | Popoff | 260/551 P |
| 3,910,969 | 10/1975 | Franz | 260/397.7 R |

*Primary Examiner*—Thomas A. Waltz
*Attorney, Agent, or Firm*—Anthony J. Franze

[57] ABSTRACT

3-[[(4-Aminophenyl)sulfonyl]amino]-N-[diaminophosphinyl]-benzamide is useful as an inhibitor of the enzyme urease as well as being an effective antimicrobial agent.

1 Claim, No Drawings

3-[[(4-AMINOPHENYL)SULFONYL]AMINO]-N-[DIAMINOPHOSPHINYL]-BENZAMIDE

This invention is concerned with chemical compounds. More particularly, it is concerned with 3-[[(4-aminophenyl)sulfonyl]amino]-N-[diaminophosphinyl]-benzamide.

This compound is a potent inhibitor of the enzyme urease. Urease is produced by a number of bacterial species particularly Proteus exemplary of which are *Proteus mirabilis, Proteus vulgaris, Proteus morganii* and *Proteus rettgeri*, all of which are well-known urinary tract pathogens. Their ability to produce urease in the urinary tract, which contains substantial amounts of urea, provides a setting wherein urease splits urea according to this scheme:

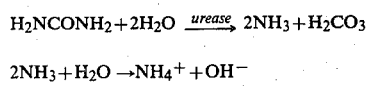

$$2NH_3 + H_2O \rightarrow NH_4^+ + OH^-$$

This reaction sequence poses a hyperammonuria and alkalinity of the urine affording a locale favorable to the formation of struvite ($MgNH_4PO_4 \cdot 6H_2O$) a predominant component of infected urinary calculi. Such struvite formation and alkalinization of the urine render the treatment of urinary tract infections difficult and oftentimes recalcitrant to otherwise effective urinary tract antiseptics.

The compound of this invention is highly effective in inhibiting urease which is intimately associated with the pathogenicity of the Proteus species of bacteria. Thus, a concentration of this compound in the amount of $2 \times 10^{-6}$ molar evinces a 50% inhibition of the urease of intact *Proteus mirabilis* cells.

The anti-urease potency of the compound of this invention was determined using intact *Proteus mirabilis* cells as the source of urease. Compounds were preincubated with *Proteus mirabilis* cells suspended in a saline solution (0.1 molar) buffered with 0.1 molar tris(hydroxymethyl)aminomethane (pH 8.0). After 40 minutes preincubation, the remaining urease activity was determined by collecting the ammonia formed in five minutes after the addition of the substrate, urea. Ammonia assays were carried out according to the procedure of Seligson and Seligson [J. Lab. Clin. Med. 38, 324–330 (1951)]. Percent inhibition was calculated by comparing the amount of ammonia generated by cells preincubated with 3-[[(4-aminophenyl)sulfonyl]amino]-N-[diaminophosphinyl]-benzamide with the controls, in which preincubation was carried out in the absence of compound.

The compound of this invention possesses antibacterial activity. It is particularly inimical to *Proteus mirabilis* and *Escherichia coli* at levels of 1.4 to $5.5 \times 10^{-5}$ molar in commonly employed in vitro techniques for determining antibacterial activity.

The antibacterial property of this compound as well as its urease inhibitory action make it useful in combatting infections of the urinary tract.

In order that this invention may be fully available to and understood by those skilled in the art, the following procedure is supplied.

A. 3-[[(4-Nitrophenyl)sulfonyl]amino]benzamide

A solution containing 44 g (0.32 m) of 3-aminobenzamide, 71.6 g (0.32 m) of p-nitrobenzenesulfonyl chloride and 700 ml of pyridine was stirred and heated on a steam bath for 2.5 hours, then poured into ice water. Acetic acid was added to a pH 5.0–6.0 and the resulting solid collected by filtration, washed with water and air-dried to give 105 g, m.p. 240°–244°.

B. N-[Dichlorophosphinyl]-3-(4-nitrobenzenesulfonylamino)benzamide

A suspension of 32.1 g (0.1 m) of 3-[[(4-nitrophenyl)sulfonyl]-amino]-benzamide and 208 g (0.1 m) of phosphorous pentachloride in a mixture of 300 ml of carbon tetrachloride and 100 ml of nitromethane was stirred and heated for 90 min. The resulting solution was cooled to 20° and 4.7 g (0.1 m) of 97% formic acid added. The reaction was stirred overnight, then the product collected by filtration, washed with carbon tetrachloride and air-dried to give 36.7 g, melts 133°–134°, solidifies 138°, melts 188°–193°.

C. N-[Diaminophosphinyl]-3-[[(4-nitrophenyl)sulfonyl]amino]benzamide

To a mixture of 19.3 g (0.044 m) of N-[(dichlorophosphinyl]-3-(4-nitrobenzenesulfonylamino)benzamide, 28.9 ml of triethylamine and 550 ml of chloroform was added anhydrous ammonia to a pH 9.0–10 while maintaining a temperature of 0°. The reaction was filtered, washed with ether and air-dried. Then the crude product was triturated in cold water, filtered and air-dried to give 16 g, softens 190°–236°, decomposes to 323°. Recrystallization of the 16 g, plus another 13.4 g previously synthesized, from 2500 ml of methanol, with charcoal, gave 22.4 g, softens 194°, some melt 210°, 246°, decomposes to 343°.

D. 3-[[(4-Aminophenyl)sulfonyl]amino]-N-[diaminophosphinyl]benzoate

Reduced with hydrogen, 18.4 g (0.046 m) of N-[diaminophosphinyl]-3-[[(4-nitrophenyl)sulfonyl]amino]benzoate in 750 ml of methanol and 2.0 g of 5% Pd/C containing 50% water. A hydrogen uptake of 9.5 psi was recorded (theoretical 9.2 psi). The catalyst was removed by filtration and the methanol filtrate evaporated in vacuo to give 18.2 g, softens, melts 114°–160°. A recrystallization from absolute alcohol, with charcoal, followed by a second recrystallization from methanol gave 7.5 g (44%), some melts 188°–190°, complete 196°.

Anal. Calcd. for $C_{13}H_{16}N_5O_4PS$: C, 42.27; H, 4.37; N, 18.97.

Found: C, 42.02; H, 4.30; N, 18.76.

What is claimed is:

1. The compound 3-[[(4-Aminophenyl)sulfonyl]amino]-N-[diaminophosphinyl]-benzamide.